(12) United States Patent
Matson

(10) Patent No.: US 6,736,972 B1
(45) Date of Patent: May 18, 2004

(54) METHOD AND SYSTEM FOR PROVIDING THERAPEUTIC AGENTS WITH HEMOFILTRATION FOR REDUCING INFLAMMATORY MEDIATOR RELATED DISEASES

(75) Inventor: James R. Matson, Dallas, TX (US)

(73) Assignee: Immunocept, L.L.C., Dallas, TX (US)

( * ) Notice: Subject to any disclaimer, the term of this patent is extended or adjusted under 35 U.S.C. 154(b) by 74 days.

(21) Appl. No.: 09/815,675

(22) Filed: Mar. 23, 2001

Related U.S. Application Data

(60) Provisional application No. 60/191,788, filed on Mar. 24, 2000.

(51) Int. Cl.$^7$ .......................... B01D 61/00; A61M 1/34; A61M 1/14; A61K 38/00
(52) U.S. Cl. ................... 210/650; 210/321.6; 210/651; 422/44; 514/1; 514/2; 604/4.01; 604/5.01; 604/5.04
(58) Field of Search ................ 210/321, 6, 321.72, 210/645, 646, 650, 651; 422/44; 514/1, 2, 12, 21; 530/380, 381, 382, 383, 384; 424/85.2; 435/2, 219, 226; 604/4.01, 5.01, 5.02, 5.04, 6.09

(56) References Cited

U.S. PATENT DOCUMENTS

| | | | |
|---|---|---|---|
| 2,682,268 A | 6/1954 | Ryan et al. ................. | 604/252 |
| 4,000,072 A | 12/1976 | Sato et al. .................. | 210/315 |
| 4,172,071 A | 10/1979 | De Maeyer et al. ........ | 260/112 |
| 4,248,736 A | 2/1981 | Fuchigami et al. ......... | 252/428 |
| 4,313,831 A | 2/1982 | Lehmann et al. ........... | 210/341 |
| 4,362,155 A | 12/1982 | Skurkovich ................. | 128/214 |
| 4,402,940 A | 9/1983 | Nose et al. .................. | 424/101 |
| 4,581,141 A | 4/1986 | Ash ............................ | 210/502 |
| 4,614,513 A | 9/1986 | Bensinger .................... | 604/6 |
| 4,787,974 A | 11/1988 | Ambrus et al. ........... | 210/321.8 |
| 4,844,810 A | 7/1989 | Richalley et al. ........... | 210/646 |

(List continued on next page.)

FOREIGN PATENT DOCUMENTS

| | | | | |
|---|---|---|---|---|
| EP | 0 098 392 A2 | 6/1983 | ........... | B01D/13/04 |
| EP | 0 787 500 A1 | 8/1997 | ............ | A61M/1/34 |
| WO | 95/04559 | 2/1995 | ............ | A61M/1/34 |

OTHER PUBLICATIONS

Konstantin et al. "Artificial Liver"from. Artificial Organs vol. 16 Issue pp. 235–242 Blackwell Publications Inc. Boston MA 1992 International Society for Artificial Organs, 1992.
"Hemodiafiltration in Two Chambers Without Replacement Fluid: A Clinical Study" by C. Sanz–Moreno and J. Botella Artificial Organs vol. 19 No. 5 1995.
International Search Report for PCT/US/99/15426, Jan. 20, 2000.
International Search Report PCT/US02/23603 5 pages, mailed Apr. 15, 2003.
International Search Report PCT/US03/07784 6 pages, mailed Jul. 17, 2003.
Seiichi Mochizuki et al.'s, "*Dextran transport through asymmetric ultrafiltration membranes: Comparison with hydrodynamic models*", Journal of Membrane Science, 68 (1992) pp. 21–41, 1992.

*Primary Examiner*—John Kim
(74) *Attorney, Agent, or Firm*—Baker Botts L.L.P.

(57) ABSTRACT

The present invention relates to a method and system for providing hemofiltration for reducing inflammatory mediator related diseases. In one form, a hemofiltration system for treating inflammatory mediator related diseases is disclosed. The system includes a hemofilter to receive blood from a specimen, the hemofilter removing selective inflammatory mediators from the blood and at least one therapeutic agent used in association with the hemofilter, the therapeutic agent to reduce adverse inflammatory mediator effects.

5 Claims, 6 Drawing Sheets

U.S. PATENT DOCUMENTS

| | | | |
|---|---|---|---|
| 4,872,983 A | 10/1989 | Dimantoglou et al. | 210/500 |
| 4,874,522 A | 10/1989 | Okamoto et al. | 210/645 |
| 4,897,189 A | 1/1990 | Greenwood et al. | 210/195 |
| 4,900,720 A | 2/1990 | Kotitschke | 514/21 |
| 5,211,850 A | 5/1993 | Shettigar et al. | 210/645 |
| 5,286,449 A | 2/1994 | Kuroda et al. | 422/48 |
| 5,450,516 A | 9/1995 | Pasquali et al. | 385/115 |
| 5,523,096 A | 6/1996 | Okarma et al. | 424/489 |
| 5,536,412 A | 7/1996 | Ash | 210/645 |
| 5,571,418 A | 11/1996 | Lee et al. | 210/651 |
| 5,683,584 A | 11/1997 | Wenthold et al. | 210/500 |
| 5,744,042 A | 4/1998 | Stange et al. | 210/645 |
| 5,762,798 A | 6/1998 | Wenthold et al. | 210/500 |
| 5,851,394 A | 12/1998 | Shibata et al. | 210/500 |
| 5,855,782 A | 1/1999 | Falkenhagen et al. | 210/323.1 |
| 5,858,238 A | 1/1999 | McRea et al. | 210/645 |
| 5,919,369 A | 7/1999 | Ash | 210/645 |
| 5,919,444 A * | 7/1999 | Norman, Jr. | 424/85.2 |
| 5,931,802 A | 8/1999 | Yoshida et al. | 604/4 |
| 5,945,337 A | 8/1999 | Brown | 435/389 |
| 6,008,199 A | 12/1999 | Grinnell et al. | 514/21 |
| 6,022,477 A | 2/2000 | Luo et al. | 210/645 |
| 6,039,946 A | 3/2000 | Strahilevitz | 424/140.1 |
| 6,042,784 A | 3/2000 | Wamsiedler et al. | 422/44 |
| 6,156,734 A | 12/2000 | Grinnell et al. | 514/21 |
| 6,193,681 B1 | 2/2001 | Davidner et al. | 604/6.08 |
| 6,287,516 B1 | 9/2001 | Matson et al. | 422/44 |

* cited by examiner

METHOD AND SYSTEM FOR PROVIDING THERAPEUTIC AGENTS WITH HEMOFILTRATION FOR REDUCING INFLAMMATORY MEDIATOR RELATED DISEASES

RELATED APPLICATION

This application claims priority from U.S. Provisional Patent Application Serial No. 60/191,788 filed Mar. 24, 2000, and entitled "Method and System for Providing Therapeutic Agents with Hemofiltration for Reducing Inflammatory mediator Related Diseases".

This application is related to copending application Ser. No. 09/858,210 filed May 15, 2001, entitled Method and System for Colloid Exchange Therapy filed by David Radunsky et al.; and copending application Ser. No. 09/912,904 filed Jul. 25, 2001, entitled Hemofiltraton Systems, Methods and Devices Used to Treat Inflammatory Mediator Related Disease filed by James R. Matson et al.

TECHNICAL FIELD

The present invention relates generally to systems, methods, and devices used for hemofiltration. More specifically, the present invention relates to hemofiltration for reducing inflammatory mediator-related diseases (IMRD), which include systemic inflammatory response syndrome ("SIRS"), multiorgan system dysfunction syndrome ("MODS"), multiorgan system failure ("MOSF"),and compensatory anti-inflammatory response syndrome (CARS).

BACKGROUND

Patients with life threatening illness are cared for in hospitals in the intensive care unit ("ICU"). These patients may be seriously injured from automobile accidents, etc., have had major surgery, have suffered a heart attack, or may be under treatment for serious infection, cancer, or other major disease. While medical care for these primary conditions is sophisticated and usually effective, a significant number of patients in the ICU will not die of their primary disease. Rather, a significant number of patients in the ICU die from a secondary complication known commonly as "sepsis" or "septic shock". Once again, the proper medical terms for sepsis and septic shock are systemic inflammatory response syndrome ("SIRS"), multiorgan system dysfunction syndrome 25 ("MODS"), multiorgan system failure ("MOSF"),and compensatory anti-inflammatory response syndrome (CARS).

In short, medical illness, trauma, complication of surgery, and, for that matter, any human disease state, if sufficiently injurious to the patient, may elicit SIRS/MODS/MOSF or CARS. The systemic inflammatory response within certain physiologic limits is beneficial. As part of the immune system, the systemic inflammatory response promotes the removal of dead tissue, healing of injured tissue, detection and destruction of cancerous cells as they form, and mobilization of host defenses to resist or to combat infection. If the stimulus to the systemic inflammatory response is too potent, such as massive tissue injury or major microbial infection, however, then the systemic inflammatory response may cause symptoms which include fever, increased heart rate, and increased respiratory rate. This symptomatic response constitutes systemic inflammatory response syndrome ("SIRS"). If the inflammatory response is excessive, then injury or destruction to vital organ tissue may result in vital organ dysfunction, which is manifested in many ways, including a drop in blood pressure, deterioration in lung function, reduced kidney function, and other vital organ malfunction. This condition is known as multiorgan dysfunction syndrome ("MODS"). With very severe or life threatening injury or infection, the inflammatory response is extreme and can cause extensive tissue damage with vital organ damage and failure. These patients will usually die promptly without the use of ventilators to maintain lung ventilation, drugs to maintain blood pressure and strengthen the heart, and, in certain circumstances, artificial support for the liver, kidneys, coagulation, brain and other vital systems. This condition is known as multiorgan system failure syndrome ("MOSF). These support measures partially compensate for damaged and failed organs, they do not cure the injury or infection or control the extreme inflammatory response which causes vital organ failures.

In recent years, it is increasingly recognized that SIRS/MODS/MOSF exists in phases. In particular, an early pro-inflammatory phase, which is recognized as SIRS, usually occurring within hours or a very few days of significant injury or infection; and a later compensatory anti-inflammatory response syndrome (CARS) which occurs later (5–10 days). SIRS and CARS also appear in repeating and alternate cycles, or concurrently.

A s noted previously, the pro-inflammatory response is critical to host recovery and survival (by healing injury and eliminating infection), but when extreme this response causes vital organ dysfunction or failure. In biology, it is common for one response to be counter balanced by another response; these compensatory responses or systems allow restoration of balance and return the organism (e.g., the patient) to homeostasis. CARS is associated with the abatement of the excess IM characteristic of SIRS, however CARS itself is often extreme and results in immune suppression. SIRS and CARS are each associated with respective characteristic IM. The immune suppression of CARS is very commonly associated with secondary infection. This secondary infection then elicits another SIRS, often worse and more destructive than the first. In patients, it is commonly this second episode of SIRS which is lethal.

Both SIRS and CARS are mediated by excesses of either pro-inflammatory and anti-inflammatory mediators, respectively. Hemofiltration should be as beneficial to CARS as to SIRS. However, in SIRS the improvement should be affirmatively observed by improvement in pulmonary and cardio-circulatory function and survival, whilst in CARS it will be observed negatively, by non-occurrence of secondary infection and secondary SIRS. Both SIRS and CARS may be monitored in a limited way, by monitoring their respective IM in blood, lung or other body fluid.

Hemofiltration with a 100 to 150 kD filter is anticipated to remove the excess circulating IM which respectively characterize SIRS/MODS/MOSF, or CARS. During either condition, it may be desirable to actually supplement IM or provide some other therapeutic agent to augment the system in abatement. In particular, during SIRS/MODS/MOSF when pro-inflammatory IM are in excess, in addition to performance of hemofiltration to remove excess pro-inflammatory IM, the administration of anti-inflammatory IM or therapeutic agents may be useful to additionally abate or otherwise modulate the pro-inflammatory systemic inflammatory response. Similarly, during CARS hemofiltration is expected to remove excess anti-inflammatory IM which should ameliorate immune suppression, in addition, administration of pro-inflammatory IM or other therapeutic agent to promote immune responsiveness, should ameliorate immune suppression of CARS. What is sought is therapeutic synergy between large pore hemofiltration and administration of appropriate therapeutic agents.

In the United States of America each year, SIRS/MODS/MOSF afflicts approximately 400,000–600,000 patients and results in about 150,000 deaths. Overall, depending on the number of organ systems failing, the mortality rate of MOSF ranges generally from 40 to 100%. For instance, if three (3) or more vital organs fail, death results in more the 90% of cases. SIRS/MODS/MOSF and CARS are the most common cause of death in intensive care units and is the thirteenth most common cause of death in the United States of America. SIRS/MODS/MOSF and CARS cost about $5 to $10 billion yearly for supportive care. In addition, the incidence of SIRS/MODS/MOSF and CARS are on the rise; reported cases increased about 139% between 1979 and 1987. This increase is due to an aging population, increased utilization of invasive medical procedures, immunosuppressive therapies (e.g. cancer chemotherapy) and transplantation procedures. (Morbidity and Mortality Weekly Report 1990; Detailed Diagnoses and Procedures, National Hospital Discharge Survey, 1993, from CDC/National 5 Center for Health Statistics, October/1995.)

The detrimental mechanism of SIRS/MODS/MOSF and CARS is the excessive activation of the inflammatory response. The inflammatory response consists of the interaction of various cell systems (e.g., monocyte/macrophage, neutrophil, and lymphocytes) and various humoral systems e.g., cytokine, coagulation, complement, and kallikrein/kinin). Each component of each system may function as an effector (e.g., killing pathogens, destroying tissue, etc.), a signal (e.g., most cytokines), or both. Humoral elements of the inflammatory response were known as toxic mediators, but are now known collectively as inflammatory mediators ("IM"). IM include various cytokines (e.g., tumor necrosis factor ("TNF"); the interleukins; interferon, etc.), various prostaglandins, various clotting factors (e.g., platelet activating factor ("PAF"), various peptidases, reactive oxygen metabolites, and various poorly understood peptides which cause organ dysfunction (myocardial depressant factor ("MDF"). These compounds interact as a network with the characteristics of network preservation and self amplification. Some of these compounds, such as MDF and peptidases, are directly injurious to tissue; other compounds, such as cytokines, coordinate destructive inflammation. Infection (e.g., abscesses and sepsis) is a common complication of critical illness. Certain bacterial exotoxins, endotoxins or enterotoxins are extremely potent stimuli to SIRS/MODS/MOSF and CARS. The development and use of effective antibiotics and other supportive measures have not had a significant effect on the death rate from MOSF. The systemic inflammatory response with its network of systems (e.g., monocyte/macrophage, complement, antibody production, coagulation, kallikrein, neutrophil activation, etc.) is initiated and regulated through the cytokine ("CK") system and IM's. The CK system consists of more than thirty known molecules each of which activates or suppresses one or more components of the immune system and one or more CK in the network. The CK network is the dominant control system of the immune response. The sources of CK's are monocyte/macrophages and endothelial cells and they are produced in every tissue in the body. Key characteristics of the CK system are as follows: (i) CK are chemical signals coordinating immune system and associated system activities; (ii) commonly, two or more CK will trigger the same action providing a "fail safe" response to a wide variety of different stimuli (the systemic inflammatory response is critical to an individual's survival; these redundant control signals assure a system response which does not falter.); (iii) CK and IM concentrations (usually measured in blood) therefore increase in order to stimulate, control, and maintain the inflammatory response proportionally to the severity of the injury or infection; and (iv) as severity of injury or infection increases, the cytodestructive activity of the system increases resulting in MODS/MOSF. Therefore, high concentrations of CK and IM measured in the patient's blood, which are sustained over time, correlate with the patients risk of death.

Major research efforts by the biotechnology industry have sought cures for SIRS/MODS/MOSF and CARS, but none to date have been licensed by the United States Food and Drug Administration ("FDA") for use in humans. There is currently no definitive therapy for SIRS/MODS/MOSF or CARS(Dellinger, 1997; Natanson, 1994), even though a great deal of research funds have been spent on failed therapies for sepsis (Knaus, 1997). Critical care medicine techniques available to manage SIRS/MODS/MOSF and CARS are generally supportive in that they do not cure SIRS/MODS/MOSF. The biotechnology industry, however, has developed a number of prospective treatments for SIRS/MODS/MOSF and CARS. The general strategy of these prospective treatments is to identify what is conceived-to be a key or pivotal single CK or IM. This single target CK or IM is then inactivated in an attempt to abate the inflammatory response. The most widely applied technologies used to inactivate CK or IM is binding with monoclonal antibodies ("MoAb") or specific antagonists ("SA"). MoAb's and SA's are used because they effectively bind the target CK or IM, or its receptor, usually in an "all or none" blockade. This strategy is problematic for two (2) reasons. First, the CK system is essential to mobilize the inflammatory response, and through it, the host immune response. If the CK system were blocked, death would ensue from unhealed injury or infection. Second, the CK and IM signals which make up the control network of the immune response consist of many redundant control loops to assure the "fail safe" initiation and continuation of this critical response. In the field of engineering, control theory indicates that a redundant, self amplifying system will not be effectively controlled by blocking one point, such as one CK or IM (Mohler, 1995).

Also, of interest, note the existing technique of hemofiltration ("HF"), which was developed as a technique to control over hydration and acute renal failure in unstable ICU patients. Existing HF techniques may use a hemofilter of some sort, which consists of cellulose derivatives or a synthetic membrane (e.g., polysulfone, polyamide, etc.) fabricated as either a parallel plate or hollow fiber filtering surface. Since the blood path to, through, and from the membrane is low resistance, the patient's own blood pressure drives blood through the filter circuit. In these HF applications, the hemofilter is part of a blood circuit. In passive flow HF, arterial blood flows through a large bore cannula, into plastic tubing leading to the filter; blood returns from the filter through plastic tubing to a vein. This is known as arteriovenous HF. Alternately, a blood pump is used, so that blood is pumped from either an artery or a vein to the filter and returned to a vein. This is known as arterio-venous HF or pumped veno-venous HF. Ultrafiltrate collects in the filter jacket and is drained through the ultrafiltrate line and discarded. Ultrafiltrate flow rates are usually 250 ml–2000 ml/hour. In order to prevent lethal volume depletion, a physiologic and isotonic replacement fluid is infused into the patient concurrently with HF at a flow rate equal to or less than the ultrafiltrate flow rate. The balance of replacement fluid and ultrafiltrate is determined by the fluid status of the patient.

The pores of most filter membranes allow passage of molecules up to 30,000 Daltons with very few membranes allowing passage of molecules up to 50,000 Daltons. The membranes used to treat renal failure were generally designed to achieve the following specific goals: (i) to permit high conductance of the aqueous phase of blood plasma water needed to permit the formation of ultrafiltrate at a fairly low transmembrane pressure (typically 20–40 mmHg), which requires a relatively large pore size that incidentally passes molecules of up to 30,000 to 50,000 Daltons; and ii) to avoid passage of albumin (e.g., 68,000 Daltons). Note that with these existing hemofilters used to treat renal failure, the ultrafiltrate contains electrolytes and small molecules (e.g., urea, creatinine, and uric acid), but no cells and only peptides and proteins smaller than the membrane pore size. The composition of the ultrafiltrate is very similar to plasma water. Loss of albumin, and subsequently, oncotic pressure, could cause or aggravate tissue edema and organ dysfunction (e.g., pulmonary edema), so hemofilters are designed to avoid this by having molecular weight exclusion limits well below the molecular weight of albumin (e.g., 68,000 Daltons).

During filtration of protein containing solutions, colloids or suspensions, or blood, the accumulation of protein as a gel or polarization layer occurs on the membrane surface. This gel layer typically reduces effective pore size, reducing the filterable molecular weights by roughly 10–40%. Therefore, pore sizes selected are somewhat larger than needed, anticipating a reduction in effective size. Thus, present membranes allow filtration and removal of excess water, electrolytes, small molecules and nitrogenous waste while avoiding any loss of albumin or larger proteins. These membranes are well-suited to their accepted uses, that is, treatment of over hydration and acute renal failure in unstable ICU patients.

Uncontrolled observations in ICU patients indicate that HF, in addition to controlling over hydration and acute renal failure, is associated with improvements in lung function and cardiovascular function. None of these improvements has been associated with a shortened course of ventilator therapy, a shortened ICU stay, or improved survival. The usual amount of ultrafiltrate removed in the treatment of over hydration and acute renal failure is 250 to 2000 ml/hour, 24 hours a day. A few published observations have suggested that higher amounts of ultrafiltrate brought about greater improvements in pulmonary and cardiovascular status; these have resulted in the development of a technique known as high volume HF ("HVHF"). In HVHF, from 2 to 9 liters/hour of ultrafiltrate are taken for periods of from 4 to 24 hours or more. Furthermore, preliminary uncontrolled or poorly controlled studies suggest that HVHF improves survival in patients with SIRS/MODS/MOSF or CARS; there is growing interest in the use of HVHF in SIRS/MODS/MOSF and CARS. There is however great hesitance to use HVHF for the following reasons: (i) the high volumes (currently 24–144 liters/day) of ultrafiltrate require equally high volumes of sterile, pharmaceutical grade replacement fluid; at these high volumes, errors in measuring ultrafiltrate coming out and replacement fluid flowing into the patient could cause injurious or lethal fluid overload or volume depletion; (ii) the high volume of ultrafiltrate removed could filter out of the blood desirable compounds from the patient resulting in dangerous deficiencies; this is currently theoretical, but should be taken seriously; (iii) large volumes of warm (body temperature) ultrafiltrate flowing out of the patient, and large volumes of cool (room temperature) replacement fluid flowing into the patient can cause thermal stress or hypothermia; and (iv) high volumes of replacement fluid add considerable expense to the therapy.

HVHF, as currently practiced, uses conventional hemofilters with pore sizes which provide a molecular weight cutoff of 30,000 Daltons and occasionally of 50,000 Daltons.

The device and process described in U.S. Pat. No. 5,571,418 generally contemplates the use of large pore hemofiltration membranes with pore sizes to provide molecular weight exclusion limits of 100,000 to 150,000 Daltons. With these higher molecular weight cutoffs, these membranes are designed to remove a wider range of different IM's; these large pore membranes should remove excess amounts of all known IM's. These large pore hemofiltration membranes have been demonstrated in animal studies to be superior to conventional hemofilter membranes in improving survival time in a swine model of lethal Staphylococcus aureus infection (Lee, P A et al. Critical Care Medicine, April 1998). It is anticipated that they will be superior to conventional membranes in SIRS/MODS/MOSF and CARS. However, it may be anticipated that in HVHF, the large pore membranes may also remove more desirable compounds thus increasing the risk of the negative side effects of HVHF.

Other techniques used in the past to treat acute renal failure and/or SIRS/MODS/MOSF and CARS include hemodialysis and plasmapheresis. Hemodialysis is well suited to fluid and small solute (less than 10,000 Daltons) removal. However hemodialysis membranes remove very few IM (only those smaller than 5000 to 10,000 Daltons) and so have been ineffective in improving a patient's condition in SIRS/MODS/MOSF and CARS. In the unstable ICU patient, hemodialysis commonly results in rapid deterioration of cardiovascular function and pulmonary function requiring premature termination of the dialysis procedure. Hemodialysis has also been associated with increasing the occurrence of chronic renal failure in survivors of SIRS/MODS/MOSF or CARS. HF was specifically developed (Kramer, 1997) to avoid these complications of hemodialysis and has been very successful in doing so.

Plasmapheresis can be done with both membrane based and centrifugation based techniques. Plasmapheresis separates plasma and all that plasma contains from blood, leaving only formed elements. The removed plasma is usually replaced by either albumin solution or fresh frozen plasma. The removed plasma would contain all IM's. Studies of plasmapheresis in animal models of SIRS/MODS/MOSF and CARS have shown increased mortality with plasmapheresis compared to untreated control animals. No controlled study of plasmapheresis in humans with SIRS/MODS/MOSF or CARS has ever been done. The expense of albumin and fresh frozen plasma, and the risk of transmission of serious or deadly viral disease with fresh frozen plasma are serious draw backs to the use of plasmapheresis in SIRS/MODS/MOSF or CARS.

Consequently, the prior art remains deficient in the lack of effective methods of treating IM related disease (e.g., SIRS/MODS/MOSF), which is safe. Furthermore, while high volume hemofiltration holds some promises, it is unworkable in its present form and is overly dangerous. Additionally, control theory suggests the concept that inhibiting a single immune mediator(IM) will not succeed in controlling SIRS/MODS/MOSF or CARS. The present invention fulfills this longstanding need and desire in this art.

SUMMARY OF THE INVENTION

In accordance with teachings of the present invention a method and system for providing therapeutic agents with hemofiltration for reducing inflammatory mediator related diseases is disclosed. The present invention is particularly beneficial when used in large pore hemofiltration systems.

According to one aspect of the present invention, a hemofiltration system for treating inflammatory mediator related diseases is disclosed. The system includes a hemofilter to receive blood from a specimen and remove selective inflammatory mediators from the blood. The system further includes at least one therapeutic agent used in association with the hemofilter to reduce adverse inflammatory mediator effects.

In a particularized form the system further includes a 100 to 150 kiloDalton hemofilter.

In a further particularized form the system includes an adsorption device associated with the hemofilter.

In another particularized form, the system includes a selective biological agent to reduce adverse inflammatory mediator effects.

In a further particularized form, the system includes a selective pharmaceutical agent to reduce adverse inflammatory mediator effects.

According to another aspect of the present invention, a method for treating inflammatory mediator related diseases is disclosed. The method includes receiving blood from a specimen, filtering the blood using a hemofilter wherein the hemofilter removes selective inflammatory mediators from the blood. The method further includes providing at least one therapeutic agent wherein the therapeutic agent reduces adverse inflammatory mediator effects.

In a particularized form, the therapeutic agent includes a biological agent.

In another particularized form, the therapeutic agent include a pharmaceutical agent.

In a further particularized form, the hemofilter is configured as a 100 to 150 kiloDalton hemofilter.

In another particularized form, an adsorptive device associated with the hemofilter is provided.

One technical advantage of the present invention includes providing rapid stabilization of the septic shock to increase survival rate of a specimen or patient.

Another technical advantage of the present invention includes abating excessive and destructive inflammatory activity which characterizes septic shock.

A further technical advantage includes increasing the effectiveness of therapeutic agents as adjunctive therapy to hemofiltration.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein.

DETAILED DESCRIPTION OF THE INVENTION

Figure 1A:
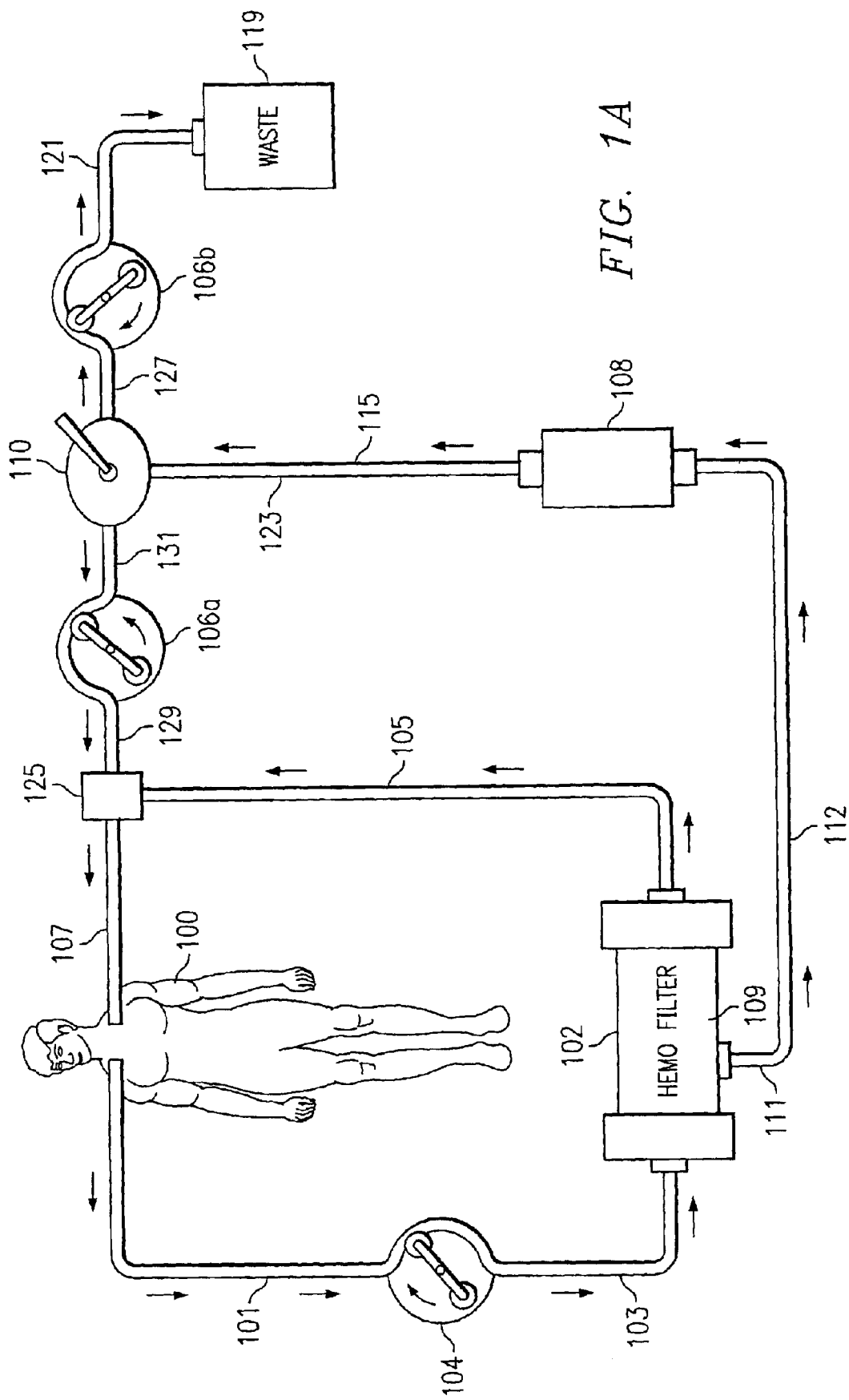
FIG. 1A illustrates a block diagram of a system for providing hemofiltration to a specimen or patient according to one embodiment of the present invention.

Preferred embodiments of the invention and its advantages are best understood by reference to FIGS. 1A–7.

As a point of reference, please note the following terms and definitions.

The term "hemofiltration" refers to a process of filtering blood by a membrane with separation of all formed elements, all proteins larger than effective pore size of the membrane, and retained plasma water and solute (these return to the patient) from ultrafiltrate.

The term "ultrafiltrate" refers to the filtered plasma water, solute and molecules (including target peptides and proteins including IM) smaller than effective pore size of the membrane.

The term "Systemic Inflammatory Response Syndrome" ("SIRS") refers to the excessive and dysfunctional elaboration by a human patient of inflammatory mediators ("IM") which results in an excessive and injurious inflammatory response.

The term "Multiple Organ Dysfunction Syndrome" ("MODS") refers to SIRS causing injury or destruction to vital organ tissue and resulting in vital organ dysfunction, which is manifested in many ways, including a drop in blood pressure, deterioration in lung function, reduced kidney function, and other vital organ malfunction.

The term "Multiple Organ System Failure" ("MOSF") refers to the clinical syndrome of vital organ dysfunction or failure due to tissue injury resulting from SIRS. The mortality rate of MOSF is approximately 40–100%.

The term "Inflammatory Mediator Related Disease" ("IMRD") refers to any disease state characterized by injurious or lethal excess production of IM. Diseases commonly included in this category include Lupus Erythematosus, Hemolytic Uremic Syndrome, Bullous Pemphigoid, pemphigus vulgaris, sepsis, SIRS/MODS/MOSF, and the like.

The term "Compensatory Anti-inflammatory Response Syndrome" ("CARS") refers to the clinical condition which occurs in association with or in response to SIRS, which is a reduction, compensatory or otherwise, of the immune responsiveness of the host. If the reduced immune responsiveness of CARS is sufficiently severe, then anergy and increased susceptibility to infection may lead to complicating new infection in the host. CARS is associated with circulating anti-inflammatory mediators (interleukins–4, –10, –11, and –13, soluble receptors of TNF, and the like); concentration of these anti-inflammatory IM in the blood of the host may correlate with the severity of CARS.

The term "Inflammatory Mediators" or "IM" refers to a heterogeneous group of chemicals synthesized and released by human tissue. IM include cytokines, prostaglandins, oxygen metabolites, kinins, complement factors, various clotting factors, various peptidases, various peptides, various proteins, and various toxic peptides. The molecular weight range of known IM is 1,000–100,000 Daltons.

The term "Hemofilter" refers to the filter used in hemofiltration. It can be configured in a number of ways, such as a series of parallel plates or as a bundle of hollow fibers. The blood path is from a blood inlet port, through the fibers or between the plates, then to a blood outlet port. Filtration of blood occurs at the membrane with ultrafiltrate forming on the side of the membrane opposite the blood. This ultrafiltrate accumulates inside the body of the filter contained and embodied by the filter jacket. This jacket has an ultrafiltrate drainage port.

Figure 1B:
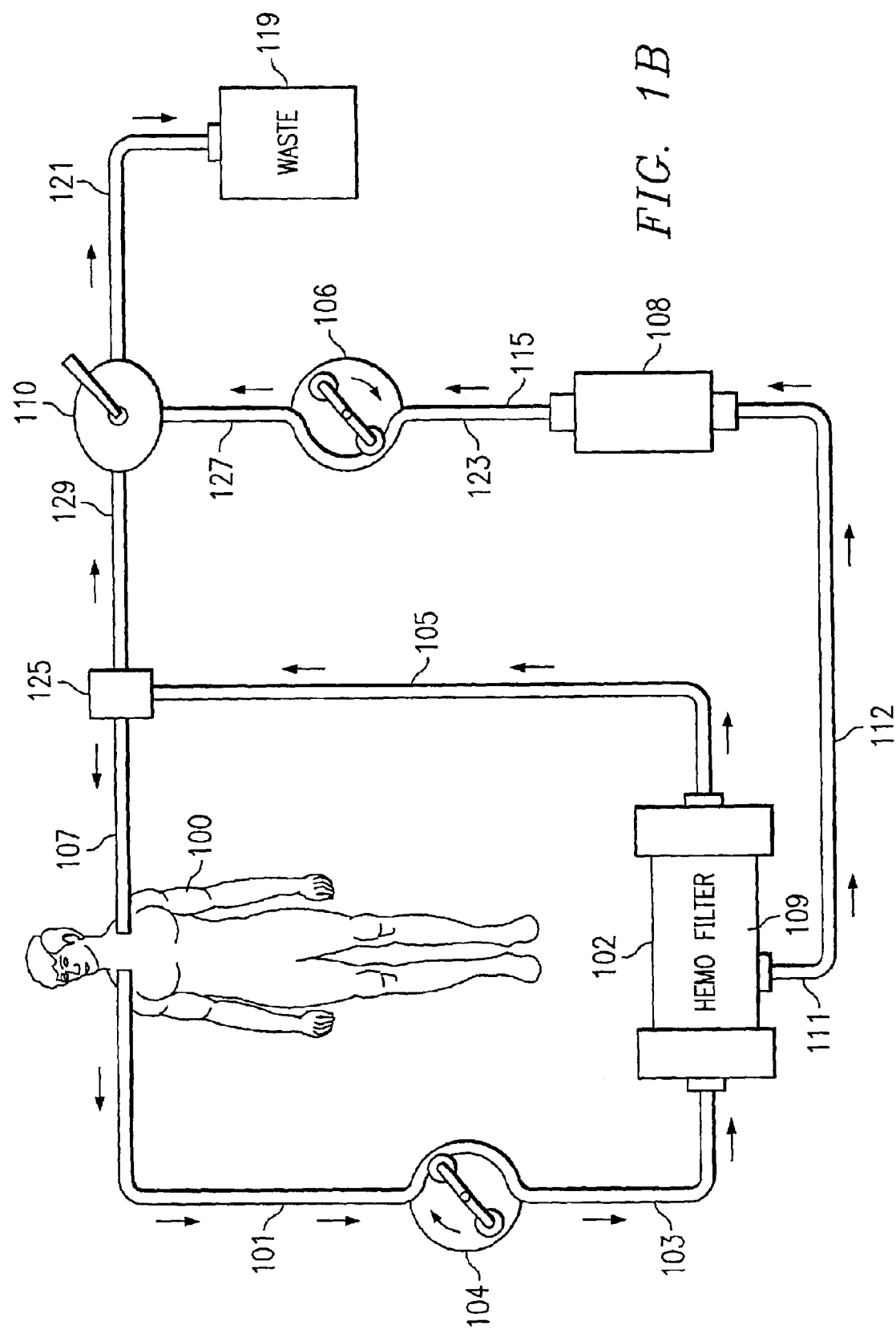
FIG. 1B illustrates a block diagram of another system for providing hemofiltration to a specimen or patient according to one embodiment of the present invention.
Figure 2:
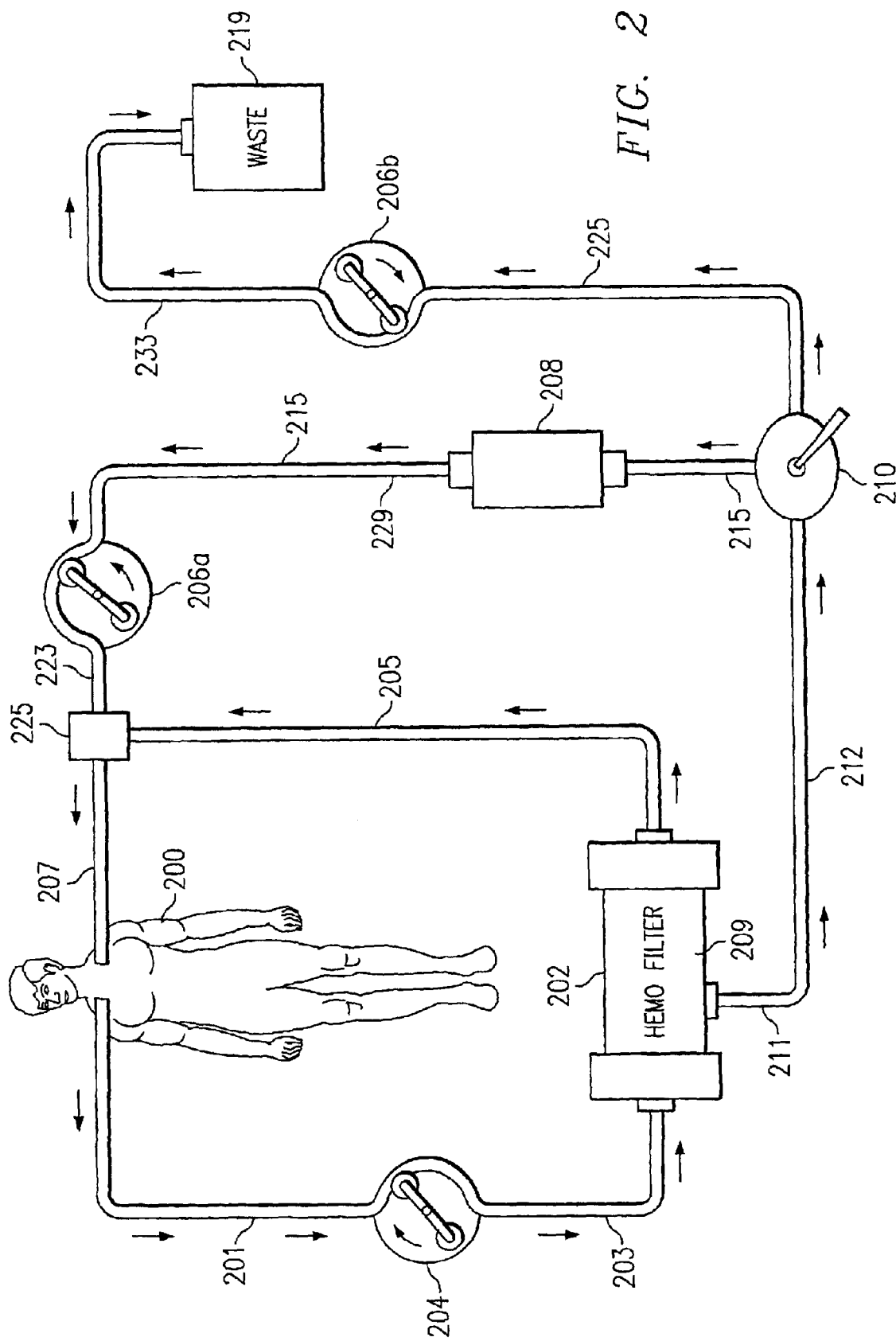
FIG. 2 illustrates a schematic of a block diagram of an alternative system for providing hemofiltration to a specimen or patient according to one embodiment of the present invention.
Figure 3:
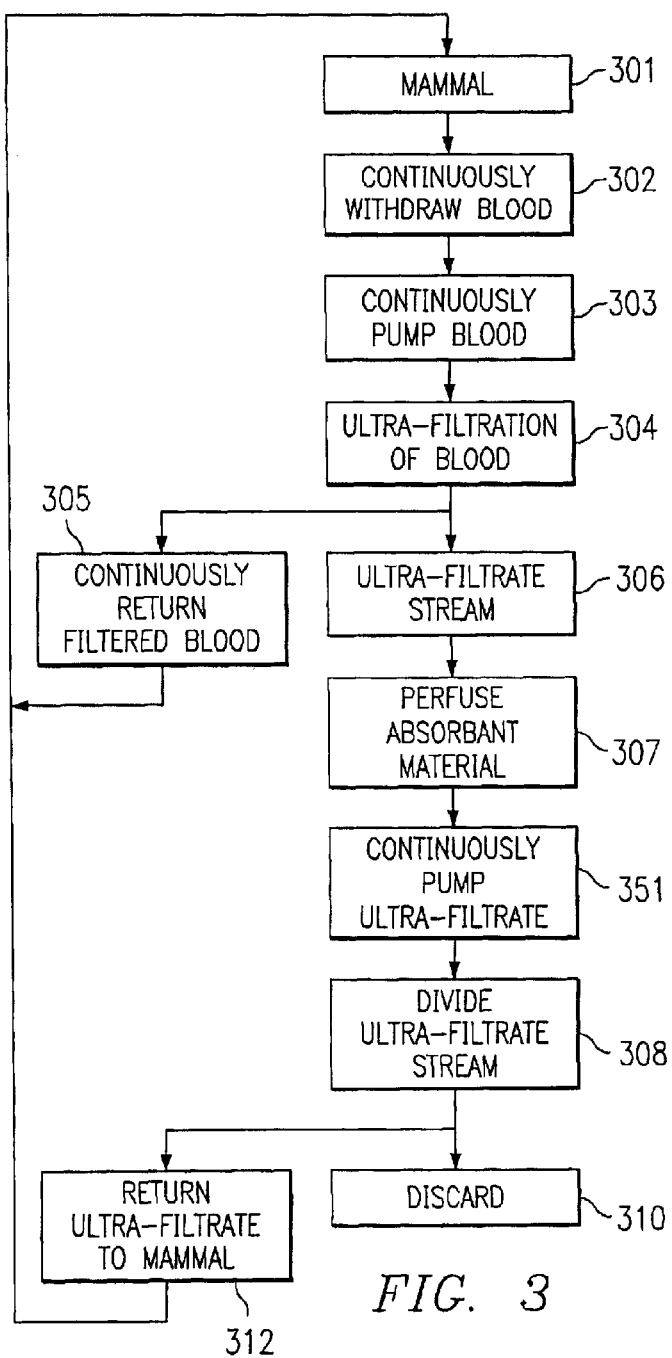
FIG. 3 illustrates a system flow diagram of the system illustrated in FIG. 1A according to one embodiment of the present invention.
Figure 4:
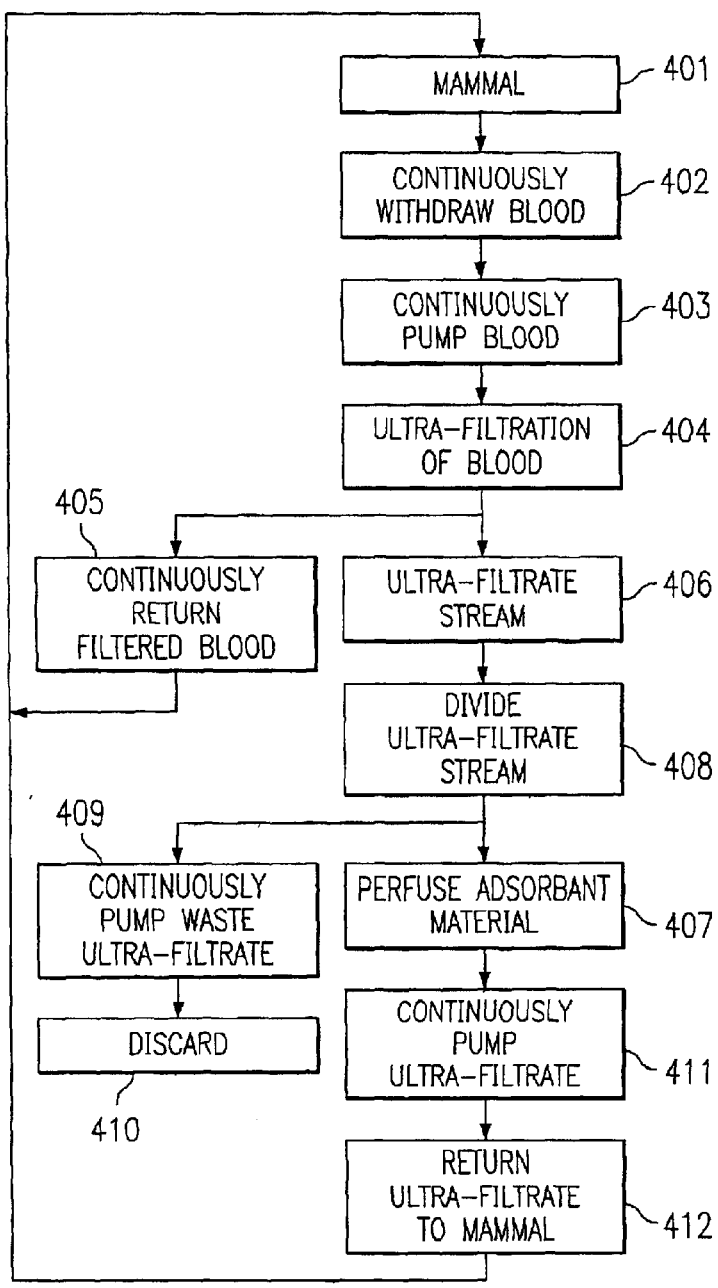
FIG. 4 illustrates a system flow diagram of the system illustrated in FIG. 2 according to one embodiment of the present invention.

FIG. 1A is a schematic of the physical layout of various components of a preferred embodiment, including specimen or patient 100, hemofilter 102, blood pump 104, first ultrafiltrate pump 106a, second ultrafiltrate pump 106b, adsorptive device 108 having one or more chambers containing adsorbent material of one or more types, three-way stop cock or first three-way joint 110, second three-way joint 125, and associated tubing. FIG. 1B is similar to FIG. 1A, except that single ultrafiltrate pump 106 is used in lieu of first ultrafiltrate pump 106a and second ultrafiltrate pump 106b. Both FIGS. 1A and 1B position three-way stop cock or first three-way joint 110 in such a manner that it divides ultrafiltrate stream downstream from adsorptive device 108. FIG. 2 is an alternate schematic of the physical layout of various components of a preferred embodiment shown in FIGS. 1A and 1B, except that three-way stop cock or first three-way joint 210 divides ultrafiltrate stream before adsorptive device 208. FIG. 3 is a diagram showing the system flow of a preferred embodiment shown in FIG. 1A. FIG. 4 is a diagram showing the system flow of a preferred embodiment shown in FIG. 2.

Steps 301 and 302 (in FIG. 3) and steps 401 and 402 (in FIG. 4) show blood being continuously withdrawn from specimen or patient 100 (in FIGS. 1A and 1B) and specimen or patient 200 (in FIG. 2) and directed to blood pump 104 (in FIGS. 1A and 1B) and blood pump 204 (in FIG. 2) via first tubing 101 (in FIGS. 1A and 1B) and first tubing 201 (in FIG. 2). Specifically, step 303 (in FIG. 3) and step 403 (in FIG. 4) show the continuous pumping of blood by blood pump 104 into hemofilter 102 via second tubing 103 (in FIGS. 1A and 113) and by blood pump 204 into hemofilter 202 via second tubing 203 (in FIG. 2). Specimen or patient 100 (in FIGS. 1A and 1B) and specimen or patient 200 (in FIG. 2), such as a human being, preferably have a major blood vessel cannulated allowing for the continuous withdrawal of blood by blood pump 104 (in FIGS. 1A and 1B) and blood pump 204 (in FIG. 2). As shown in steps 304 and 306 (in FIG. 3) and steps 404 and 406 (in FIG. 4), hemofilter 102 ultra-filters blood extracted from specimen or patient 100 (in FIGS. 1A and 1B) and hemofilter 202 102 ultra-filters blood extracted from specimen or patient 200 (in FIG. 2). And, step 305 (in FIG. 3) and step 405 (in FIG. 4) returns blood filtered by hemofilter 102 to specimen or patient 100 via third tubing 105 and fourth tubing 107 in FIGS. 1A and 1B and by hemofilter 202 to specimen or patient 200 via third tubing 205 and fourth tubing 207 in FIG. 2.

Referring to FIGS. 1A, 1B, and 2, ultrafiltration is a filtration process in which blood cells and blood proteins with a molecular size larger than the pore size of hemofilter membrane 109 (in FIGS. 1A and 1B) and hemofilter membrane 209 (in FIG. 2) are retained in the blood path. The composition of hemofilter membrane 109 (in FIGS. 1A and 1B) and hemofilter membrane 209 (in FIG. 2) are preferably comprised of biocompatible material, such as polysulfone, polyacrylonitrile, polymethylmethacrylate, polyvinyl-alcohol, polyamide, polycarbonate, cellulose derivatives, etc., but is not limited to these materials. The jacket of the hemofilter will be preferably comprised of a biocompatible material, such as polycarbonate, but not limited to, polycarbonate. Hemofilter membrane 109 (in FIGS. 1A and 1B) and hemofilter membrane 209 (in FIG. 2) are preferably organized as a parallel plate membrane or as a membrane hollow fiber. Preferred Embodiments use a hemofilter incorporating the techniques and materials discussed in U.S. Pat. No. 5,571,418 discusses the use of large pore hemofiltration membranes for hemofiltration processes. Hemofilter membrane 109 in FIGS. 1A and 1B and hemofilter membrane 209 in FIG. 2 are preferably comprised of large pore hemofiltration membranes, which are preferably fabricated from any biocompatible material suitable for the purpose such as polysulfone, polyacrylonitrile, polymethylmethacrylate, polyvinyl-alcohol, polyamide, polycarbonate, cellulose derivatives, etc., but, of course, without limitation to these materials.

As shown in step 304 in FIG. 3, hemofilter membrane 109 (in FIGS. 1A and 1B) sieves a fraction of plasma water, electrolytes, blood peptides and proteins with a molecular size smaller than the pore size of the membrane to form ultrafiltrate stream 111 (in FIGS. 1A and 1B), which is directed to adsorptive device 108 (in FIGS. 1A and 1B), which has one or more chambers containing adsorbent material of one or more types, via fifth tubing 112 (in FIG. 1A and 1B). As shown in step 307 in FIG. 3, adsorptive device 108 is perfused by ultrafiltrate stream 111. Similarly, as shown in step 404 in FIG. 4, hemofilter membrane 209 (in FIG. 2) sieves a fraction of plasma water, electrolytes, blood peptides and proteins with a molecular size smaller than the pore size of the membrane to form ultrafiltrate stream 211 (in FIG. 2), which is directed to adsorptive device 208 (in FIG. 2), which has one or more chambers containing adsorbent material of one or more types, via fifth tubing 212, and sixth tubing 215 (in FIG. 2). As shown in step 407 in FIG. 4, adsorptive device 208 is perfused by ultrafiltrate stream 211.

As shown in steps 308 in FIG. 3, ultrafiltrate stream 115 (in FIGS. 1A and 1B) is divided at three-way stop cock or first three-way joint 110 (in FIGS. 1A and 1B), after adsorptive device 108 in FIG. 1A and 1B. As shown by step 408 in FIG. 4, ultrafiltrate stream 211 (in FIG. 2) is divided at three-way stop cock or first three-way joint 210 (in FIG. 2), before adsorptive device 208 in FIG. 2.

Specifically, in FIG. 1A, after three-way stop cock or first three-way joint 110 divides post-adsorptive ultrafiltrate stream 115, discard ultrafiltrate stream 127 is directed toward second ultra-filtrate pump 106b and to waste reservoir 119 and return ultrafiltrate stream 131 is directed toward first ultra-filtrate pump 106a and on to specimen or patient 100. In FIG. 1B, ultrafiltrate stream 115 is directed toward single ultrafiltrate pump 106 and discard ultrafiltrate stream 121 is directed to waste reservoir 119 and return ultrafiltrate stream 129 is returned to specimen or patient 100. In FIG. 2, ultrafiltrate stream 211 is directed toward three stop cock 210 and discard ultrafiltrate stream 221 is directed toward second ultrafiltrate pump 206b and then onto waste reservoir 219 and return ultrafiltrate stream 229 is directed toward first ultrafiltrate pump 206a and eventually returned to specimen or patient 200.

Figure 5A:
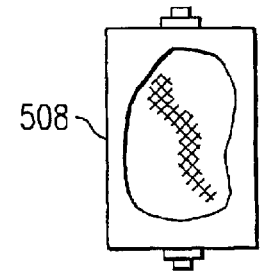
FIG. 5A, 5B, and 5C are diagrams showing alternate embodiments of adsorbent devices.
Figure 5B:
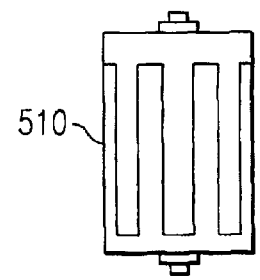
Figure 5C:
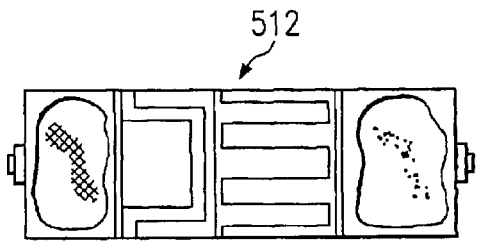

Adsorptive device 108 (in FIGS. 1A and 1B) and adsorptive device 208 (in FIG. 2) may have one or more chambers containing adsorbent material(s). The adsorbent material(s) is (are) preferably included within the respective adsorbent device and none will pass into the ultrafiltrate stream or return to specimen or patient 100 (in FIGS. 1A and 1B) and specimen or patient 200 (in FIG. 2). The adsorbent materials used in the preferred embodiment may be coated or uncoated. The nature of the adsorbent materials used in the preferred embodiment is such that solutes to be adsorbed will be bound to the adsorbent materials. As shown in FIG. 5A, 5B, and 5C, adsorbent material is presented to ultrafiltrate flow by structures such as rods or plates, or flows through structures such as beads or porous matrix of any configuration effective in presentation of adsorptive material (s) to ultrafiltrate stream, or flows through one or more chambers containing immobilized particulate, beaded or fragmented adsorbent material. Adsorbent materials may include, but are not limited to: silica, activated charcoal, nonionic resins, ionic resins, immobilized polymyxin B, anion exchange resin, cation exchange resin, neutral exchange resin, immobilized monoclonal antibodies, immobilized IM receptors, immobilized specific antagonists, cellulose and its derivatives, synthetic materials (e.g., polysulfone, polyacrylonitrile, polymethylmethacrylate, polyvinyl-alcohol, polyamide, polycarbonate, etc.) and the like or any combination thereof. The selection of adsorbent materials depends on the inflammatory mediators to be removed. Preferred embodiment uses polymyxin to remove endotoxin, anti-TNF antibody to remove TNF, polyacrylonitrile to remove interleukin 1-beta and TNF, among other adsorbents, both specific and nonspecific. Adsorbents may also be used in various combinations as the patients condition and stage of disease warrant.

FIGS. 5A, 5B, and 5C are diagrams showing preferred embodiments of adsorptive device 108 (in FIG. 1A and 1B) and adsorptive device 208 (in FIG. 2), both of which have one or more chambers containing adsorbent material of one or more types. Adsorbent materials vary widely in their adsorptive capacity, and types and conditions of substances adsorbed. IM are of many different chemical types (e.g. peptides, lipids) and each IM's charge and plasma binding (e.g., specific or nonspecific circulating soluble receptors) will vary the characteristics of how they may be adsorbed during the course of any inflammatory mediator related disease ("INIRD") or episode of SIRS/MODS/MOSF and CARS. For this reason, various adsorbent materials will be used in order to provide the range of chemical binding characteristics and capacity needed for removal of many IM from ultrafiltrate. As stated above, adsorbent materials are of different chemical and physical types. Particulate adsorbent materials (e.g. charcoal; beads of polysulfone, polyacrylonitrile, polymethylmethacrylate, polyvinyl-alcohol, polyamide, polycarbonate, cellulose derivatives, and similar materials; liposortes, etc.) may be coated or uncoated, but are usually encased in a porous flexible mesh sac or rigid porous containment jacket which allows free access of perfusing fluid (e.g. ultrafiltrate) but contains the particles and prevents them from being carried back to the specimen or patient in the ultrafiltrate stream. Some adsorbents (e.g. silica gel) lend themselves to being cast or otherwise fabricated in various rigid or semirigid configurations (e.g. rods, plates etc.) which allow for effective and convenient presentation of ultrafiltrate containing IM to the adsorbent material. Some adsorbents (e.g. monoclonal antibodies, IM receptors, specific antagonists, polymyxin B) will need to be affixed to a supporting matrix of biocompatible material (e.g. polycarbonate and the like) for presentation of adsorbent material to the ultrafiltrate stream containing IM. The matrix of biocompatible material will be configured to allow effective and convenient presentation of ultrafiltrate containing IM to the affixed adsorbent material.

Depending on physical and chemical compatibilities of the adsorbent materials, and the requirements of adequate ultrafiltrate flow, adsorbent device 108 (in FIGS. 1A and 1B) and adsorbent device 208 (in FIG. 2) may be configured as one chamber containing one or more adsorbent materials, as shown in adsorptive device 508 in FIG. 5A and adsorptive device 510 in FIG. 5B, or separated into multiple chambers each containing one or more adsorbent materials, as shown in adsorptive device 512 in FIG. 5C. Adsorbent devices 508 (in FIG. 5A), 510 (in FIG. 5B), and 512 (in FIG. 5C) have an inlet port to which the ultrafiltrate tubing which carries tile ultrafiltrate from hemofilter 108 (in FIGS. 1A and 1B) and hemofilter 208 (in FIG. 2) will be attached to provide ultrafiltrate flow to adsorbent devices 508, 510, or 512. Ultrafiltrate flow through adsorbent device 508 (in FIG. 5A), 510 (in FIG. 5B), and 512 (in FIG. 5C), perfuses the adsorbent materials allowing for adsorption of IM, and flows out of the adsorbent device through an outlet port.

Referring to FIG. 5C, where a multiple chamber configuration is used for adsorptive device 512, the chambers will be separated by a screen or other porous barrier which retains the adsorbent materials or combinations of adsorbent materials in their separate compartments and allows free flow of ultrafiltrate through adsorptive device 512. An alternative embodiment utilizes separate, exchangeable modules each containing an adsorbent material or adsorbent materials. A module or a combination of modules may be inserted into the adsorbent device to provide for the adsorption of different types of IM as the condition of the specimen or patient may require. Although not shown, adsorbent device 108 (in FIGS. 1A and 1B) and adsorptive device 208 (in FIG. 2) can be incorporated into or combine with hemofilter 102 (in FIGS. 1A and 1B) and hemofilter 202 (in FIG. 2), respectively. In this embodiment ultrafiltrate formed at the hemofilter membrane will pass into the hemofilter jacket, the hemofilter jacket will incorporate the adsorptive materials in one or more chambers and ultrafiltrate will flow through the adsorbent materials. Ultrafiltrate will transfer from the combined hemofilter/adsorbent device through an outlet port to post adsorbent ultrafiltrate tubing.

The amount of blood continuously pumped will be operator determined and depend on the condition of specimen or patient 100 (in FIGS. 1A and 1B) and specimen or patient 200 (in FIG. 2) and the needs of effective HF. The amount of blood continuously removed must be determined on a case by case basis. The flow rate, the amount of blood removed and the duration of the HF therapy are determined by the weight, the age and the nature and severity of illness of specimen or patient. Typically, blood flow rates range from 100 to 200 ml/minute. The rate of ultrafiltration depends on the nature and severity of illness and is indexed to body weight, total body water and/or clinical indices of disease management (e.g., pulmonary function, cardiovascular status, etc.). Typically, total ultrafiltrate flow rate is 1 to 9 liters/hour of which from 0 to 2 liters/hour may be discarded. The discard rate will be determined by the fluid balance requirements of the specimen or patient. The amount of ultrafiltrate discarded will be determined by operator as operator judges the needs of specimen or patient 100 and specimen or patient 200 for fluid removal. All ultrafiltrate not discarded is returned to specimen or patient 100 (in FIGS. 1A and 1B) and specimen or patient 200 (in FIG. 2).

With respect to the tubing used in preferred embodiments for tubing, the composition of the material making up the blood pump tubing, ultrafiltrate tubing, etc, is preferably of a biocompatible material, such as polyvinylchloride, but not limited to this material. The tubing will be flexible and have outside diameters complementary to the appropriate hemofilter connections, adsorptive device connections, joints, stop cocks, or pump heads.

Specifically, with respect to the tubing in FIG. 1A, first tubing 101 transfers blood from specimen or patient 100 to blood pump 104, second tubing 103 transfers blood from blood pump 104 to hemofilter 102; third tubing 105 transfers the filtered blood filtered by hemofilter 102 to second three-way joint 125; fourth tubing 107 transfers the filtered blood along with the post adsorption ultrafiltrate to specimen or patient 100; fifth tubing 112 transfers the ultrafiltrate to adsorptive device 108; sixth tubing 123 transfers the post adsorption ultrafiltrate to three-way stop cock or second three-way joint 110; seventh tubing 131 transfers post adsorption ultrafiltrate to first ultrafiltrate pump 106a; eighth tubing 129 transfers post adsorption ultrafiltrate from first ultrafiltrate pump 106a to second three-way joint 125 joining fourth tubing 107 which transfers filtered blood along with the post adsorption ultrafiltrate to the specimen or patient; ninth tubing 127 transfers post adsorption ultrafiltrate to second ultrafiltrate pump 106b; and tenth tubing 121 transfers post adsorption ultrafiltrate from second ultra filtrate pump 106b to waste reservoir 119. First ultrafiltrate pump 106a and associated tubing implement steps 311 and 312 in FIG. 3; second ultrafiltrate pump 106b, waste reservoir 119, and associated tubing implement steps 309 and 310 in FIG. 3.

With respect to the tubing in FIG. 1B, first tubing 101 transfers blood from specimen or patient 100 to blood pump 104; second tubing 103 transfers blood from blood pump 104 to hemofilter 102; third tubing 105 transfers the filtered blood filtered by hemofilter 102 to second three-way joint 125; fourth tubing 107 transfers the filtered blood along with the post adsorption ultrafiltrate to specimen or patient 100; fifth tubing 112 transfers the ultrafiltrate to adsorptive device 108; sixth tubing 123 transfers the post adsorption ultrafiltrate or ultrafiltrate stream 115 to single ultrafiltrate pump 106; seventh tubing 127 transfers post adsorption ultrafiltrate from ultrafiltrate pump 106 to three-way stop cock or first three-way joint 110; eighth tubing 129 transfers post adsorption ultrafiltrate from three-way stop cock or first three-way joint 110 to second three-way joint 125 joining fourth tubing 107 which transfers filtered blood along with the post adsorption ultrafiltrate to specimen or patient 100; and ninth tubing 121 transfers post adsorption ultrafiltrate from three-way stop cock or first three-way joint 110 to waste reservoir 119. Single ultrafiltrate pump 106 and associated tubing transfer post adsorption ultrafiltrate; waste reservoir 119 and associated tubing discard undesirable waste; second three-way joint 125 and associated tubing transfer filtered blood along with post adsorption ultrafiltrate to specimen or patient 100.

With respect to the tubing in FIG. 2, first tubing 201 transfers blood from specimen or patient 200 to blood pump 204; second tubing 203 transfers blood from blood pump 204 to hemofilter 202; third tubing 205 transfers the filtered blood filtered by hemofilter 202 to second three-way joint 225; fourth tubing 207 transfers the filtered blood along with the post adsorption ultrafiltrate to specimen or patient 200; fifth tubing 212 transfers the ultrafiltrate to three-way stop cock or first three-way joint 210; sixth tubing 215 transfers the ultrafiltrate from three-way stopcock or first three-way joint 210 to adsorptive device 208; seventh tubing 229 transfers the post adsorption ultrafiltrate or ultrafiltrate stream 215 to first ultrafiltrate pump 206a; eighth tubing 223 transfers post adsorption ultrafiltrate from first ultrafiltrate pump 206a to second three-way joint 225 joining fourth tubing 207 which transfers filtered blood along with the post adsorption ultrafiltrate to specimen or patient 200; ninth tubing 225 transfers ultrafiltrate from three-way stop cock or first three-way joint 210 to second ultrafiltrate pump 206b; and tenth tubing 233 transfers ultrafiltrate from second ultrafiltrate pump 206b to waste reservoir 219. First ultrafiltrate pump 206a and associated tubing implement steps 411 and 412 in FIG. 4; second ultrafiltrate pump 206b and waste reservoir 219 and associated tubing implement steps 409 and 410 in FIG. 4.

Figure 6:
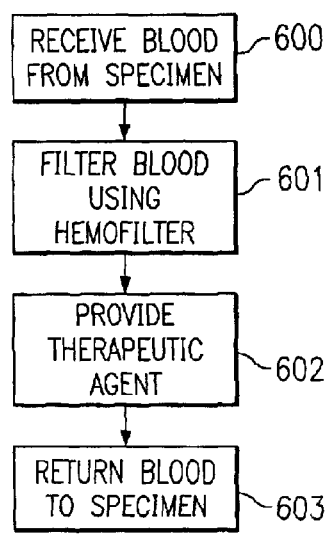
FIG. 6 illustrates a method for providing therapeutic agents with hemofiltration according to one embodiment of the present invention.

FIG. 6 illustrates a method for providing therapeutic agents with hemofiltration according to one embodiment of the present invention. The method may be used with one of the systems disclosed in FIGS. 1A, 1B, 2, and 7, or other systems configurable to provide therapeutic agents and hemofiltration.

The method begins at step 600 where a system receives blood from a specimen such as a patient. In one embodiment, blood is continuously withdrawn from a specimen or patient, preferably from a major blood vessel cannulated thereby allowing continuous withdrawal of blood from a specimen or patent. A pump may also be provided for continuous withdrawal and transfer of blood from a specimen or patient. The method then proceeds to step 601 where a hemofilter filters the blood. Hemofiltration as disclosed above includes ultrafiltration of blood extracted from a specimen or patient. Ultrafiltration is a filtration process in which blood cells and blood proteins with a molecular size larger than the pore size of the hemofilter are retained. A fraction of plasma water, electrolytes, blood peptides and proteins with a molecular size smaller than the pore size of the hemofilter remain in the bloodstream forming an ultrafiltrate.

In a preferred embodiment, the hemofilter used to filter blood includes a large pore hemofiltration membrane configured to provide molecular weight exclusion limits of 100,000 to 150,000 Daltons. In this manner, a wide range of different immune mediators can be removed from the blood.

Other embodiments may include incorporating an adsorptive device at step 601. Adsorptive devices, such as those disclosed above, may be provided for adsorbing additional IM's. An adsorptive device may be configured with one or more chambers and may be included within a hemofilter or provided as an additional component within a hemofiltration system. The adsorption device's chambers preferably include selective adsorbent materials having adsorptive characteristics and capacities for adsorbing during the course of any inflammatory mediator related disease or episode of SIRS/MODS/MOSF or CARS. Therefore, various adsorbent materials may be used in order to provide a range of chemical binding characteristics and capacities needed for removal of many IM's from ultrafiltrate.

Upon filtering the blood, the method proceeds to step 601 where a therapeutic agent is provided to the filtered blood. The therapeutic agent may be provided or integrated into the blood in certain dose adjusted amounts thereby providing a therapeutic agent in association with hemofiltration of blood.

In one embodiment, a therapeutic agent may be a pharmaceutical agent developed to treat SIRS/MODS/MOSF and CARS. Pharmaceutical agents may include, but are not limited to, allopurinol, elastase inhibitors, and prostaglandin inhibitors. Other pharmaceutical agents may be used as they are developed and become available. The pharmaceutical agent may be provided in a predetermined dosage amount such that, upon providing the pharmaceutical agent an effective amount of therapy is provided to a specimen or patient. In this manner, hemofiltration used in conjunction with a pharmaceutical agent reduces undesirable effects or disorders in an inflammatory response of a specimen or patient.

In another embodiment, the therapeutic agent may be activated protein C sometimes referred to as recombinant activated protein C. The therapeutic agent may also be a PC such as human protein C or other species and derivatives having full protein C proteolytic, amidolytic, esterolytic and biological (anticoagulant or profibrinolytic) activities. See U.S. Pat. No. 6,008,199 entitled "Methods For Treating Hypercoagulable States Or Acquired Protein C Deficiency."

In still another embodiment, the therapeutic agent may be a biological agent developed to treat SIRS/MODS/MOSF or CARS. Biological agents may include, but are not limited to, monoclonal antibodies or receptor antagonists such as antitumor necrolysis or necrosis factor, interleukin 1 receptor antagonist, and various endotoxin antibodies. Other biological agents may be used as they are developed and become available. The biological agent may be provided in a predetermined dosage amount such that, upon providing the biological agent, an effective amount of therapy is provided to a specimen or patient. In this manner, hemofiltration used in conjunction with a biological agent reduces undesirable effects or disorders in an inflammatory response of a specimen or patient.

Upon providing a therapeutic agent to the blood, the method then proceeds to step 603 where the blood is returned to a specimen or patient. Therefore, the method of FIG. 6 provides hemofiltration of blood received from a specimen or a patient. The hemofiltration is used in conjunction with a therapeutic agent, such as a pharmaceutical agent and/or a biological agent, thereby providing enhanced therapy of SIRS/MODS/MOSF and CARS. In this manner, excessive and destructive inflammatory activity can be abated allowing the inflammatory system of a specimen or patient to return to a more physiologic level.

Figure 7:
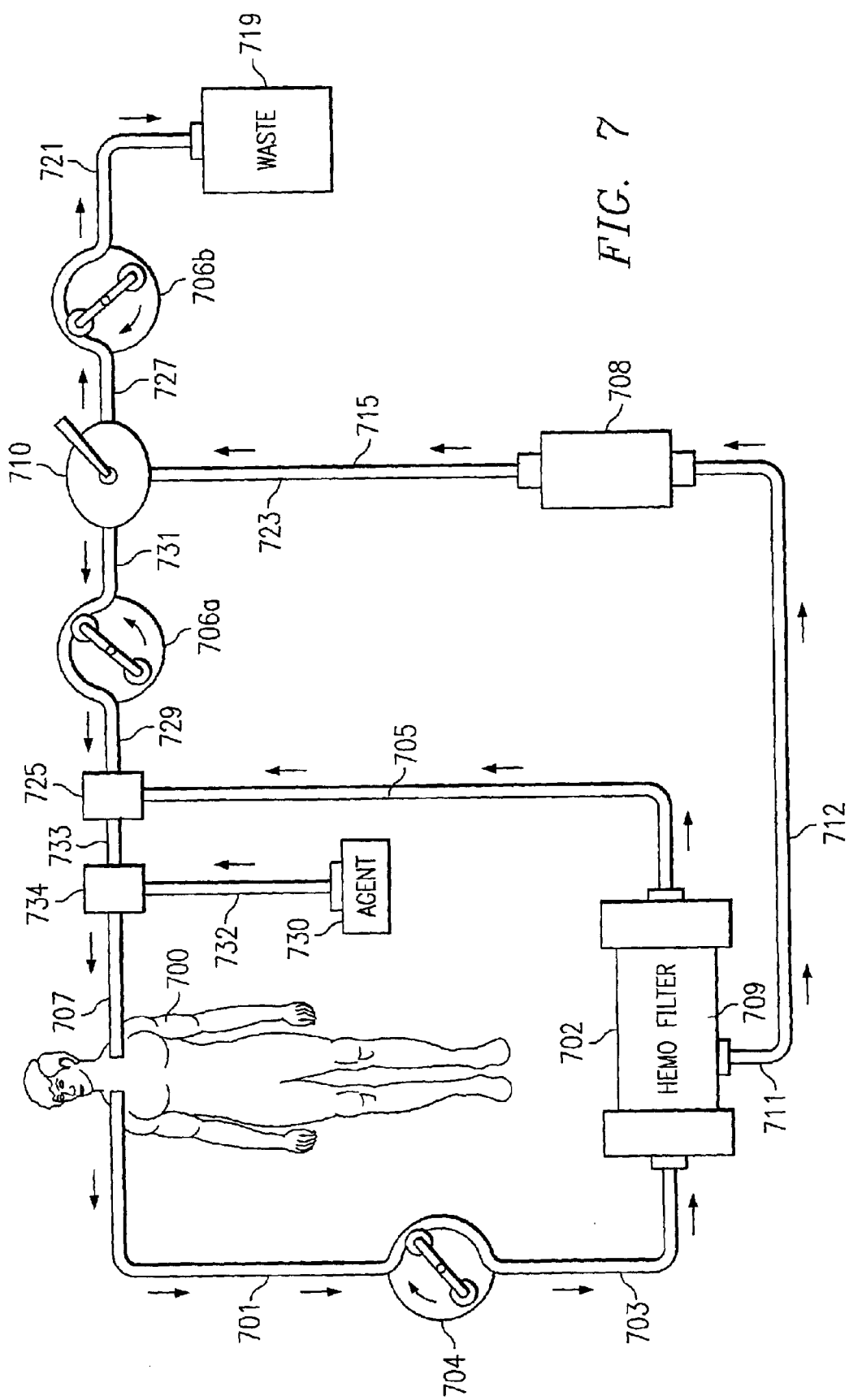
FIG. 7 illustrates a system for providing therapeutic agents and hemofiltration according to one embodiment of the present invention.

FIG. 7 illustrates a system for providing hemofiltration with therapeutic agents according to one embodiment of the present invention. The system illustrated in FIG. 7 is similar to the systems illustrated in FIGS. 1A, 1B, and 2 and may include like or similar components or features. FIG. 7 illustrates one configuration of providing a hemofiltration system incorporating therapeutic agents for providing enhanced therapy of SIRS/MODS/MOSF and CARS.

During operation, blood may be continuously withdrawn from specimen or patient 700 into tube 701 via a cannulated major blood vessel allowing continuous withdrawal of blood by blood pump 704. The amount of blood continuously pumped may depend on the condition of specimen or patient 700 and must be determined on a case by case basis.

Blood is transferred from specimen of patient 700 to hemofilter 702 via tube 701, blood pump 704 and tube 703. Tube 705 transfers the filtered blood to first three-way joint 725. Tube 712 coupled to hemofilter 702 transfers ultrafiltrate 711 to adsorptive device 708 where, via tube 723, adsorptive device transfers post adsorptive ultrafiltrate 715 to three-way stop cock 710. Three-way stopcock 710 allows transfer of post absorption ultrafiltrate 715 to first ultrafiltrate pump 706a via tube 731 and second ultrafiltrate pump 706b via tube 727. Second ultrafiltrate pump 706b and tube 721 transfer post adsorption ultrafiltrate from second ultrafiltrate pump 706b to waste reservoir 719.

First ultrafiltrate pump 706a pumps post adsorption. ultrafiltrate 715 to first three-way joint 725 via tube 731 and tube 729. First three-way joint 725 transfers filtered blood and post adsorption filtrate 715 to second three-way joint 734. Therapeutic agent 730 is transferred to second three-way joint via tube 732 where tube 707 transfers therapeutic agent 730, post adsorption ultrafiltrate 715 and blood to specimen or patient 700. In this manner, the system illustrated in FIG. 7 id provides hemofiltration of blood from a specimen or a patient in conjunction with a therapeutic agent thereby providing enhanced therapy of SIRS/MODS/MOSF and CARS.

In a preferred embodiment, hemofilter 702 may include a large pore hemofiltration membrane configured to provide molecular weight exclusion limits of 100,000 to 150,000 Daltons. In this manner, a wide range of different immune mediators can be removed from the blood.

Additionally, in a preferred embodiment therapeutic agent 730 may provide variable dose adjusted pharmaceutical agents and/or biological agents as needed by specimen or patient 700. In one embodiment, a therapeutic agent may be a pharmaceutical agent developed to treat SIRS/MODS/MOSF and CARS. Pharmaceutical agents may include, but are not limited to, allopurinol, elastase inhibitors, and prostaglandin inhibitors. Other pharmaceutical agents may be used as they are developed and become available. The pharmaceutical agent may be provided in a predetermined dosage amount such that, upon providing the pharmaceutical agent an effective amount of therapy is provided to a specimen or patient.

In another embodiment, the therapeutic agent may be a biological agent developed to treat SIRS/MODS/MOSF and CARS. Biological agents may include, but are not limited to, monoclonal antibodies or receptor antagonists such as antitumor necrolysis or necrosis factor, interleukin 1 receptor antagonist, and various endotoxin antibodies. Other biological agents may be used as they are developed and become available. The biological agent may be provided in a predetermined dosage amount such that, upon providing the biological agent, an effective amount of therapy is provided to a specimen or patient. Therefore, as different types or new therapeutic agents become available, the system illustrated in FIG. 7 may be configured to provide the newly available therapeutic agents with hemofiltration thereby providing an enhanced therapy of SIRS/MODS/MOSF and CARS.

In one embodiment, a therapeutic agent can be provided to specimen or patient 700 without the use of therapeutic agent 730, tube 732, second three-way joint 734, and tube 707. For example, a predetermined dosage amount of a therapeutic agent can be intravenously provided to specimen or patient 700 using an separate therapeutic agent system (not shown) configured to provide therapeutic agents in association with hemofiltered blood. In this embodiment, patient 700 may receive hemofiltered blood via tube 700 and variable dose adjusted therapeutic agents via a separate tube (not shown). In this manner, a hemofiltration system may be provided in addition to a therapeutic agent system for providing enhances therapy of SIRS/MODS/MOSF and CARS.

Although the invention has been described with reference to a specific embodiment, this description is not meant to be construed in a limiting sense. The example embodiments shown and described above are only intended as an example. Other applications of the preferred embodiments may be found as well. Various modifications of the disclosed embodiment as well as alternate embodiments of the invention will become apparent to persons skilled in the art upon reference to the description of the invention. For example, the hemofilters employed by the present invention may be are modified to remove a variety of selected molecules from a patient's blood in accordance with the teachings of the present invention. Additionally, the structural modification could include the integration of hemofilter 102 in FIGS. 1A and 1B and hemofilter 202 in FIG. 2 with adsorptive device 108 (in FIGS. 1A and 1B) and adsorptive device 208 (in FIG. 2), both of which have one or more chambers containing adsorbent material of one or more types, with elimination of the additional tubing. In this embodiment ultrafiltrate formed in jacket of hemofilter 102 (in FIGS. 1A and 1B) and hemofilter 202 (in FIG. 2) would be presented directly to adsorbent material contained with in hemofilter jacket or in a chamber or chambers directly contiguous with hemofilter jacket. The chamber containing ultrafiltrate would be drained by ultrafiltrate line. Ultrafiltrate would be continuously pumped and apportioned for discard or returned to specimen or patient 100 (in FIGS. 1A and 1B) and specimen or patient 200 (in FIG. 2). In addition, it is possible to modify the configuration of ultrafiltrate lines to provide for infusion of ultrafiltrate into specimen or patient 100 (in FIGS. 1A and 1B) or specimen or patient 200 (in FIG. 2) via a vascular cannula in a blood vessel arid separate from tile hemofiltration circuit. Furthermore, note the ultrafiltrate return pump and the ultrafiltrate discard pump in the preferred embodiment shown and discussed above may be combined into a single two head ultrafiltrate pump system. Also, note while the ultrafiltrate return pump and the ultrafiltrate discard pump are shown in the figures as two separate pumps, it is within the scope of the invention to combine two pumps into a single pump, and thus, the separate pumps may be interpreted as two parts of a single pump.

Modifications of adsorbent device will be determined by the inflammatory mediator related disease (IMRD) to be treated and the phase of the disease. Various regions of the IM network are dominant at different phases of an IMRD and different IMRD exhibit different patterns of IM networking. Thus a different adsorbent material or materials, or different groupings of adsorbent materials will be needed for different IMRD's in their different phases. Thus different adsorbent devices will be developed as more is learned of IMRD's and their phases. Adsorbent devices may contain a fixed adsorbent material or a fixed combination of adsorbent materials. Alternatively, an adsorbent device may be configured with different, interchangeable modules of adsorbent materials to be adapted to the changing dominance of the IM network. The modules may consist of one or more chambers containing adsorbent material of one or more types. The adsorbent device may be designed to accept modules of adsorbent materials inserted in place as dictated by patient need and operator assessment.

Different configurations of adsorbent materials will be used. Adsorbent materials exhibit chemical characteristics which determine what physical form will provide the greatest stability in flowing ultrafiltrate. Adsorbent material must remain irreversibly bound to its supporting matrix, or in the case of beads (e.g. polysulfone, polyacrylonitrile, etc) or particulates (e.g. charcoal)inescapably contained in mesh or other in containment device. Adsorbent material, matrix, and containment material can not be allowed to dissolve, dissociate or fragment into the ultrafiltrate to be infused into the specimen or patient. Adsorbent material, matrix, and containment material must be configured to provide physical durability, and adequate porosity and configuration for optimal presentation of adsorbent material to flowing ultrafiltrate. Some configurations of matrix are shown in FIGS. 5A, 5B, and 5C. Adsorbent devices of one or more chambers containing adsorbent material of one or more types could be used in series, in which ultrafiltrate flows from the first to subsequent adsorbent devices. The sequence, number and type of adsorbent devices would be determined by operator to meet the needs of specimen or patient. Alternatively, the ultrafiltrate stream could be divided by a manifold with distribution of ultrafiltrate to adsorbent devices arranged in a parallel configuration, with each line from each adsorbent device either returned to a manifold and reunited into a single ultrafiltrate line, or each line individually apportioned for return to specimen or patient and discard.

Thus, even though numerous characteristics and advantages of the present inventions have been set forth in the foregoing description, together with details of the structure and function of the inventions, the disclosure is illustrative only, and changes may be made in the detail, especially in matters of shape, size and arrangement of the parts within the principles of the inventions to the full extent indicated by the broad general meaning of the terms used in the attached claims. Accordingly, it should be understood that the modifications and variations suggested above and below are not intended to be exhaustive. These examples help show the scope of the inventive concepts, which are covered in the appended claims. The appended claims are intended to cover these modifications and alternate embodiments.

In short, the description and drawings of the specific examples above are not intended to point out what an infringement of this patent would be, but are to provide at least one explanation of how to make and use the inventions contained herein. The limits of the inventions and the bounds of the patent protection are measured by and defined in the following claims.

What is claimed is:

1. A hemofiltration system for treating inflammatory mediator related diseases, the system comprising:
   a hemofilter operable to receive blood from a specimen and to selectively remove inflammatory mediators from the blood;
   at least one therapeutic agent selected from the group consisting of allopurinol, elastase inhibitors and prostaglandin inhibitors;
   the at least one therapeutic agent used in association with the hemofilter to treat an inflammatory mediator disease selected from the group consisting of systemic inflammatory response syndrome, multiorgan system dysfunction syndrome, multiorgan system failure and compensatory anti-inflammatory response syndrome; and
   the therapeutic agent operable to reduce adverse inflammatory mediator effects.

2. The system of claim 1, wherein the hemofilter comprises a 100 to 150 kiloDalton hemofilter.

3. A method for treating inflammatory mediator related diseases, the method comprising:
   receiving blood from a specimen;
   filtering the blood using a hemofilter, to remove selective inflammatory mediators from the blood;
   providing at least one therapeutic agent to the blood to reduce adverse inflammatory mediator effects associated with treating an inflammatory mediator disease selected from the group consisting of systemic inflammatory response syndrome, multiorgan system dysfunction syndrome, multiorgan system failure and compensatory anti-inflammatory response syndrome; and the therapeutic agent comprises a pharmaceutical agent selected from the group consisting of allopurinol, elastase inhibitors and prostaglandin inhibitors.

4. A hemofiltration system for treating inflammatory mediator related diseases, the system comprising:

a hemofilter operable to receive blood from a specimen and to selectively remove inflammatory mediators from the blood;

the hemofilter comprising a 100 to 150 kiloDalton hemofilter;

the hemofilter associated with an adsorptive device;

at least one therapeutic agent used in association with the hemofilter to treat an inflammatory mediator disease selected from the group consisting of systemic inflammatory response syndrome, multiorgan system dysfunction syndrome, multiorgan system failure and compensatory anti-inflammatory response syndrome;

the therapeutic agent operable to reduce adverse inflammatory mediator effects; and the therapeutic agent-selected from the group consisting of allopurinol, elastase inhibitors and prostaglandin inhibitors.

5. A method for treating inflammatory mediator related diseases, the method comprising:

receiving blood from a specimen;

filtering the blood using a bemofilter to remove selective inflammatory mediators from the blood; and providing at least one therapeutic agent, selected from the group consisting of allopurinol, elastase inhibitors and prostaglandin inhibitors, to the blood to reduce adverse inflammatory mediator effects associated with treating an inflammatory mediator disease selected from the group consisting of systemic inflammatory response syndrome, multiorgan system dysfinction syndrome, multiorgan system failure and compensatory anti-inflammatory response syndrome.

* * * * *